United States Patent [19]

Linnoila et al.

[11] Patent Number: 5,109,007
[45] Date of Patent: Apr. 28, 1992

[54] ATTENUATION OF ETHYL ALCOHOL INTOXICATION WITH ALPHA-2 ADRENOCEPTOR ANTAGONISTS

[75] Inventors: Markku Linnoila; Richard G. Lister; Michael J. Durcan, all of Bethesda, Md.

[73] Assignee: The United States of America as represented by the Department of Health and Human Services, Washington, D.C.

[21] Appl. No.: 521,835

[22] Filed: May 10, 1990

Related U.S. Application Data

[62] Division of Ser. No. 294,119, Jan. 6, 1989, Pat. No. 4,968,692.

[51] Int. Cl.$^5$ .............................................. A61K 31/44
[52] U.S. Cl. ................................... 514/294; 514/280; 514/397; 514/411
[58] Field of Search .............. 514/396, 280, 294, 397, 514/411, 811

[56] References Cited

U.S. PATENT DOCUMENTS

4,968,692 11/1990 Linnoila .............................. 514/396
5,015,654 5/1991 Al-Damluji ......................... 514/402

OTHER PUBLICATIONS

Yamanaka, K. et al., Eur J Pharmacol 106(3): 625–628, 1984 (Abstract).
Cattier-Humblet, C. et al., Eur J Med Chem Chim Ther 20(3): 251–255, 1985 (Abstract).
The Merck Index, 11th Edition, 1989; p. 1006 #10011.
E. S. Vizi et al., The J. of Pharm. & Exp. Therap., vol. 238, No. 2, pp. 701–706 1986.
C. A. Halliday et al., Br. J. Pharmacol., vol. 95, p. 751 (1988).
A. D. Michael et al., Br. J. Pharmacol., vol. 74, pp. 255–256 (1981).
Fumiyoshi Ishikawa, Chem. Pharm. Bull., vol. 28 (1980), pp. 1394–1402.
N. Lattimer et al., N. S. Arch. Pharm.; 1984, vol. 327, pp. 31214 318.
J. C. Doxey et al., Br. J. Pharmac. (1983), vol. 78, pp. 489–505.

*Primary Examiner*—Frederick E. Waddell
*Assistant Examiner*—Diane Gardner
*Attorney, Agent, or Firm*—Birch, Stewart, Kolasch & Birch

[57] ABSTRACT

A method is provided for attenuating the intoxicating effects of ethyl alcohol in a patient, by administering to a patient in need thereof, an alpha-2 adrenoceptor antagonist compound. Two preferred compounds useful in the present invention, each being a highly potent and selective alpha-2 adrenoceptor antagonist, are atipamezole and idazoxan.

4 Claims, No Drawings

ATTENUATION OF ETHYL ALCOHOL INTOXICATION WITH ALPHA-2 ADRENOCEPTOR ANTAGONISTS

This application is a divisional of copending application Ser. No. 07/294,119 filed on Jan. 6, 1989, now U.S. Pat. No. 4,968,692.

BACKGROUND OF THE INVENTION

The present invention is generally concerned with providing a method of attenuating the effects of ethyl alcohol intoxication in a patient. Currently, when intoxicated individuals are brought into an emergency room, they are sometimes given valium. Valium is a sedating tranquilizer and therefore it adds to the effects of ethanol which is a depressant.

SUMMARY OF THE INVENTION

Accordingly, one object of the present invention is to provide a drug for treating ethanol intoxication which sobers up the patient. Another object is to provide a drug for treating ethanol intoxication which has minimal side effects.

The method of attenuating ethyl alcohol intoxication of the present invention comprises administering to an intoxicated patient, in need thereof, an effective intoxication attenuating amount of a compound having alpha-2 adrenoceptor antagonist properties.

More specifically, the method comprises administering to an intoxicated patient in need thereof, an effective intoxication attenuating amount of a highly potent and selective alpha-2 adrenoceptor antagonist such as:

a) atipamezole, i.e., 4(5)-(2,3-dihydro-2-ethyl-1H-inden-2-yl)imidazole or a pharmaceutically effective salt thereof, or b) idazoxan, i.e., 2-(2-(1,4-benzodioxanyl))-2-imidazoline or a pharmaceutically acceptable salt thereof.

DETAILED DESCRIPTION OF THE INVENTION

The term "atipamezole" as used herein means 4(5)-(2,3-dihydro-2-ethyl-1H-inden-2-yl)imidazole. A method for the preparation of atipamezole is provided for in U.S. Pat. No. 4,689,339 issued to Karjalainen, et al on Aug. 5, 1987 (see Example 11).

The term "atipamezole hydrochloride" means the hydrochloride acid addition salt of atipamezole.

The term "idazoxan" as used herein means "2-(2-(1,4-benzodioxanyl))-2-imidazoline". A method for the preparation of idazoxan is provided in British Patent No. 2,068,376, and in European Patent No. 33655.

The term "idazoxan hydrochloride" as used herein refers to the hydrochloride acid addition salt of idazoxan.

The term "pharmaceutically acceptable salt" as used herein includes acid addition salts, hydrates, alcolates and other salts which are physiologically compatible in man. The acid addition salts may be formed by either strong or weak acids. Representative of strong acids are hydrochloric, sulfuric and phosphoric acids. Representative of weak acids are fumaric, maleic, succinic, oxalic, citric, tartaric, cyclohexamic and the like.

The term "unit dosage form" as used herein refers to physically discrete units suitable as unitary dosages for human subjects, each unit containing a predetermined quantity of an alpha-2 adrenoceptor antagonist encompassed by the present invention in an amount sufficient to produce the desired effect in association with a pharmaceutically acceptable diluent, carrier or vehicle.

Both atipamezole and idazoxan have been shown to possess potent and selective alpha-2-adrenoceptor antagonist properties. Additionally, their alpha-2 adrenoceptor antagonist properties were compared by H. Scheinin, et al, Eur. J. Pharmacol., Vol. 151, p. 35–42 (1988), incorporated herein by reference. While both compounds are effective in the method of the present invention, atipamezole is approximately 100 times more selective as an alpha-2 adrenoceptor antagonist than is idazoxan.

This 100 fold difference in the two compounds selectively as alpha-2 adrenoceptors antagonist provides evidence that compounds having a range of selectivities as alpha-2 adrenoceptor antagonists will be useful in the present invention. Preferably, however, one would desire that an alpha-2 adrenoceptor antagonist, useful in the present invention, to be about at least as selective as idazoxan, which as noted herein is a potent and selective alpha-2 adrenoceptor antagonist.

Other compounds having alpha-2 adrenoceptor antagonist properties which may be useful in accordance with the present invention include idazoxan related compounds [Reckitt & Colman]Doxey, et al., Br. J. Pharmacol., Vol. 78, p. 489–505 (1983); imiloxan [Syntex] Michel, et al., Br. J. Pharmacol., Vol. 74, p. 255–256 (1981); WY 26703 (i.e., N-((2β,11bα)-1,3,4,6,7,11b-hexahydro-2H-benzo[a]-quinolizin-2-yl)-N-methylisobutanesulfonamide) and related compounds [Wyeth] Latimer, et al., Naunyn Schmiedeberg's Arch. Pharmacol., Vol. 327, p. 312–318 (1984); CH-38083 (i.e., 7,8-(methylenedioxi)-14α-hydroxyalloberbane hydrochloride) [Chinoin] Vizi, et al., J. Pharmacol. Exp. Ther., vol. 238, p. 701–706 (1986); GR 50360A (i.e., ±5-fluoro-2,3,3a,9a,-tetrahydro-1H-[1,4]-benzodioxino[2,3-c]pyrrole hydrochloride) and related compounds [Glaxo] Halliday, et al., Br. J. Pharmacol., vol. 95, p. 715 (1988); DG 5128 and related compounds of Daiichi Seiyaku Co., Ltd., Tokyo, Japan; and Yohimbine [Sigma].

The following preparations, and the pharmacological tests outlined are to be considered as exemplary of the present invention, but should not be considered to limit it.

PREPARATION I 4-(5)-(2,3-Dihydro-2-ethyl-1H-inden-2-yl)imidazole hydrochloride [1:1]

Atipamizole HCl

The compound was provided by Farmos Group Ltd. (Finland), and was used in the pharmacological test procedures outlined, infra.

PREPARATION II 2-(2-(1,4-Benzodioxanyl))-2-imidazoline hydrochloride [1:1]

Idazoxan HCl

The compound was provided by Reckitt and Colman Ltd. (England) and was used in the pharmacological test procedures outlined, infra.

Pharmacological Tests

1. Methods

Drugs. Atipamezole HCl and Idazoxan HCl were dissolved in distilled water in all experiments.

Animals. In all experiments NIH Swiss mice were used. They weighed approximately 23g and were housed in groups of 10 and maintained on a 12/12 h light/dark cycle with ad lib access of food and water.

Apparatus. The holeboard apparatus was made of Plexiglas (40×40×30 cm) and had four holes 3 cm in diameter equally spaced in the floor. Infra-red photocells in the walls of the box and directly beneath each hold provided automated measures of locomotor activity (number of beam interruptions) and of the number of head-dips made.

Holeboard exoeriment. Atipamezole (0, 1 or 3 mg/kg) and ethanol (0 or 2 g/kg) were administered i.p. contralaterally 30 min before an 8 min holeboard test.

To examine the role of pharmacokinetic factors in the interaction of atipamezole with ethanol. Separate groups of mice (n=10 per group were sacrificed 30 min after treatment with ethanol (2 g/kg) in combination with atipamezole (3 mg/kg) or its vehicle, and blood alcohol concentrations determined using Sigma diagnostics procedure 332-UV.

Intoxication study. In the test of intoxication, NIH Swiss mice were treated with ethanol (2.4 g/kg) and 5 min later their intoxication was rated using a variation of the scale of E. Majchrowicz, *Psychopharmacologia*, Vol. 43, p. 245-254 (1975). The following scores were assigned: 0=no observable effect; 1=mild ataxia; 2=moderate ataxia; 3=severe ataxia; 4=very severe ataxia-barely able to recover righting reflex; 5=loss of righting reflex. Immediately after the first rating, mice received atipamezole (0, 1 or 3 mg/kg) and were rated every 5 min thereafter for a further 20 min by an observer who was unaware of the drug treatment each animal had received. The timing between ethanol administration and testing was shorter in this study than in the holeboard experiment because of the rapid change in intoxication scores that takes place within 30 min of ethanol treatment.

In a second experiment, the effect of atipamezole was compared with that of idazoxan (1 mg/kg).

Loss of righting reflex. The effect of pretreating mice with atipamezole or idazoxan on the duration of loss of righting reflex caused by a high dose of ethanol (3.5 g/kg) was also examined. Mice received atipamezole or idazoxan 10 min before ethanol. A mouse was taken to have regained its righting reflex when it was unable to right itself on three occasions within a 60 s period.

Seizure threshold. In the final experiment the effects of atipamezole and idazoxan on the anticonvulsant effect of ethanol were examined. Separate groups of mice received atipamezole or idazoxan 5 min after treatment with ethanol (0 or 2.4 g/kg) to parallel the treatment schedule used in the intoxication studies. Fifteen minutes after the second injection seizure threshold to biculline was determined by infusion through the tail vein by the method of D. J. Nutt et al, *Brain Res.*. Vol. 413, p. 193-196 (1987). Seizure threshold was calculated from the latency to the onset of repeated myoclonic jerking of head and forelimbs.

2. Results

Holeboard experiment. There was a significant ethyl alcohol/atipamezole interaction in the analysis of the number of head dips observed ($F(2.46)=4.9$, $P<0.05$). Furthermore, while ethyl alcohol reduced exploratory head-dipping ($p<0.01$), atipamezole (which had alone failed to alter exploration) significantly reversed the decrease in exploration caused by ethyl alcohol ($p<0.01$). It was also determined that while ethyl alcohol significantly increased locomotor activity in test mice ($F(1.46)=7.12$, $p<0.001$), and that atipamezole would not alter this effect. Lastly, it was determined that atipamezole did not alter blood ethyl alcohol concentrations when compared with test mice receiving only vehicle, thus showing atipamezole's effects on mouse exploration was pharmacodynamic rather than pharmacokinetic.

Intoxication. Although test groups did not differ in their sensitivity to ethyl alcohol prior to drug treatment, atipamezole (1 mg/kg) significantly reduced ($p<0.05$) intoxication scores at 15 and 20 minutes after administration of ethyl alcohol to test mice, when compared to those receiving vehicle. Idazoxan (1 mg/kg) significantly reduced intoxication scores at 15 minutes ($p<0.01$) and 20 min ($p<0.05$) after administration of ethyl alcohol to test mice, when compared with those receiving vehicle. Significance testing was done utilizing Dunnett's test.

Loss of righting reflex. While neither alpha-2 adrenoceptor antagonist prevented the loss of righting reflex caused by the ethanol, both compounds significantly reduced the period during which the righting reflex was absent as shown in Table 1.

TABLE 1

The duration of loss of righting reflex of different groups of NIH Swiss mice following treatment with 3.5 g/kg ethanol. Mice were treated with a) atipamezole (0, 1.0 or 3.0 mg/kg) or b) atipamezole (0.3 or 1.0 mg/kg), idazoxan (0.3 or 1.0 mg/kg) or the vehicle 10 min before receiving the ethanol. Values are means+SEM (standard error of the mean).

| | n | Duration of loss of righting reflex (min) |
|---|---|---|
| (a) Vehicle | 22 | 38.6 ± 2.4 |
| Atipamezole (1.0 mg/kg) | 20 | 25.7 ± 1.8** |
| Atipamezole (3.0 mg/kg) | 23 | 26.9 ± 2.3** |
| (b) Vehicle | 12 | 39.3 ± 2.6 |
| Atipamezole (0.3 mg/kg) | 11 | 32.5 ± 3.7 |
| Atipamezole (1.0 mg/kg) | 12 | 28.5 ± 2.7* |
| Idazoxan (0.3 mg/kg) | 12 | 24.3 ± 2.2** |
| Idazoxan (1.0 mg/kg) | 10 | 29.8 ± 2.6* |

Significantly different from vehicle-treated animals,
*$p < 0.05$,
**$p < 0.01$ (Dunnett's test).

Seizure threshold. Ethanol exerted a significant anticonvulsant action, raising seizure threshold to bicuculline ($F(1.75)=581$, $p<0.0001$). Neither atipamezole (1 mg/kg and 3 mg/kg) nor idazoxan (1 mg/kg) alone showed any indication of lowering lowering seizure threshold to bicuculline, and neither drug reduced the anticonvulsant action of ethanol.

Shortly after these experiments were completed a report appeared in which several alpha-2 adrenoceptor antagonists were proconvulsant against bicuculline-induced seizures, A. Fletcher et al., *Eur. J. Pharmacol.*, Vol. 151, p. 27-34 (1988). We therefore examined the effects of higher doses of atipamezole and idazoxan on the seizure threshold to bicuculline in the present paradigm. Three groups of mice received atipamezole (10 mg/kg), idazoxan (10 mg/kg) or the vehicle 15 min prior to determining seizure threshold to bicuculline. As can be seen in Table 2, this high dose of atipamezole caused a very slight but significant reduction in seizure threshold to bicuculline ($p<0.05$). The reduction in seizure threshold caused by idazoxan failed to reach significance.

TABLE 2

The seizure threshold to bicuculline (mg/kg) of NIH Swiss mice 15 min after treatment with atipamezole, idazoxan or the distilled water vehicle. Values are means±SEM.

|  | N | Seizure Threshold |
|---|---|---|
| Vehicle | 8 | 0.448 ± 0.013 |
| Atipamezole (10 mg/kg) | 8 | 0.401 ± 0.012* |
| Idazoxan (10 mg/kg) | 10 | 0.415 ± 0.013 |

*Significantly different from vehicle-treated mice, $p < 0.05$, Dunnett.

3. Discussion

The preceding pharmacological test results show that alpha-2 adrenoceptor antagonist, and more specifically, atipamezole HCl and idazoxan HCl exhibit properties which may make them of value to those wishing to attenuate the intoxicating effects of ethyl alcohol in a patient, e.g., doctors in an emergency room. It should be noted, however, that alpha-2 adrenoceptor antagonist encompassed by the present invention most probably will not effect chronic toxicity problems associated with long-term ethyl alcohol use and/or abuse in an individual, inasmuch as compounds encompassed in the present invention do not appear to effect blood ethyl alcohol level, but only modulate intoxicated behavior.

PHARMACEUTICAL COMPOSITIONS

In practicing the method of the present invention, alpha-2 adrenoceptor antagonist will most preferably be administered to a patient in a pharmaceutical composition by combination with appropriate pharmaceutically acceptable carriers or diluents, and may be formulated into preparations in solid, semisolid, liquid or gaseous forms such as tablets, capsules, powders, granules, ointments, solutions, suppositories, injections, inhalants, and aerosols in the usual ways for their respective route of administration. The following methods and excipients are merely exemplary and are in no way limiting.

In pharmaceutical dosage forms, the alpha-2 adrenoceptor antagonist encompassed by the present invention may be used alone or in appropriate association, as well as in combination with other pharmaceutically active compounds.

In the case of oral preparations, the compounds may be used alone or in combination with appropriate additives to make tablets, powders, granules or capsules, e.g., with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethylcellulose; with lubricants such as talc or magnesium stearate; and if desired, with diluents, buffering agents, moistening agents, preservatives and flavoring agents.

Furthermore, the alpha-2 adrenoceptor antagonist encompassed by the present invention may be made into suppositories by mixing with a variety of bases such as emulsifying bases or water-soluble bases.

The alpha-2 adrenoceptor antagonist encompassed by the present invention may be formulated into preparations for injections by dissolving, suspending or emulsifying them in an aqueous or non-aqueous solvent, such as vegetable oil, synthetic aliphatic acid glycerides, esters of higher aliphatic acids or propylene glycol; and if desired, with conventional additives such as solubilizers, isotonic agents, suspending agents, emulsifying agents, stabilizers and preservatives.

In the cases of inhalations or aerosol preparations, alpha-2 adrenoceptor antagonist encompassed by the present invention, in the form of a liquid or minute powder, may be filled up in an aerosol container with gas or liquid spraying agents, and if desired, together with conventional adjuvants such as humidifying agents. They may also be formulated as pharmaceuticals for non-pressurized preparations such as in a nebulizer or an atomizer.

The amount of the compounds of the present invention to be used may vary according to the degree of the intoxication encountered and the mode of administration. When a patient is unconscious, a preferred route of administration would be by injection, and suitable dosage by injection (e.g., intramuscular or intravenous) is thought to be about 0.01 to 10.0 mg/kg body weight, preferably 0.05 to 5.0 mg/kg body weight, and most preferably 0.1 to 1.0 mg/kg body weight. The preferred dosage is of course that amount sufficient to attenuate intoxication.

The method of the present invention can generally be practiced by oral ingestion of one of the alpha-2 adrenoceptor antagonist encompassed by the present invention with a pharmaceutically acceptable carrier. The alpha-2 adrenoceptor antagonist encompassed by the present invention can also be administered systemically, e.g., parenterally, via inhalation, or rectally to a person infected with retro virus.

In unit dosage forms for oral administration such as syrups, elixirs, and suspensions (wherein each dosage unit, e.g., teaspoonful, tablespoonful, contains a predetermined amount of an active ingredient to be administered to a patient in need thereof) inclusion of pharmaceutically acceptable excipients are readily known by those skilled in the art. Parenteral administration of the alpha-2 adrenoceptor or antagonists encompassed by the present invention can be by a pharmaceutically acceptable carrier, such as Sterile Water for Injection, USP, or by normal saline.

The alpha-2 adrenoceptor antagonists encompassed by the present invention can also be administered rectally via a suppository. The suppository can include vehicles such as cocoa butter, carbowaxes and polyethylene glycols, which melt at body temperature, yet are solidified at room temperature.

The alpha-2 adrenoceptor antagonist compounds encompassed by the present invention can be utilized in aerosol formulation to be administered via inhalation. The compounds can be formulated into pressurized aerosol containers together with a pharmaceutically acceptable propellants such as dichlorodifluoromethane, propane, nitrogen and the like.

The specifications for the unit dosage forms of the present invention depend on the particular compound employed and the ethyl alcohol attenuation effect to be achieved and the pharmacodynamics associated with each compound in the host.

It is to be understood that the scope of the present invention is only to be limited by the scope of the appended claims.

What is claimed is:

1. A method of attenuating ethyl alcohol intoxication, which method comprises administering to an intoxicated patient in need thereof, an effective intoxication attenuating amount of a compound having alpha-2 adrenoceptor antagonist properties; the compounds atipamezole or idazoxan and pharmaceutically acceptable salts thereof, being excluded by proviso.

2. The method of claim 1, wherein said compound is administered in an amount of 0.01 to 10.0 mg/kg of the patient's body weight.

3. A method of attenuating ethyl alcohol intoxication, which method comprises administering to an intoxicated patient in need thereof, an effective intoxication attenuating amount of a compound having alpha-2 adrenoceptor antagonist properties, selected from the group consisting of:
  imiloxan;
  yohimbine;
  N-((2$\beta$, 11b$\alpha$)-1,3,4,6,7,11b-hexahydro-2H-benzo[a]-quinolizin-2-yl)-N-methylisobutanesulfonamide;
  7,8-(methylenedioxi)-14-$\alpha$-hydroxyalloberbane hydrochloride;
  ±5-fluoro-2,3,3a,9a,-tetrahydro-1H-[1,49-benzodioxino-[2,3,-c]pyrrole hydrochloride;
and the pharmaceutically acceptable salts thereof.

4. The method of claim 3, wherein said compound is administered in an amount of 0.01 to 10.0 mg/kg of the patient's body weight.

* * * * *